US010381108B2

(12) United States Patent
Zhou et al.

(10) Patent No.: US 10,381,108 B2
(45) Date of Patent: Aug. 13, 2019

(54) WEB SEARCH AND INFORMATION AGGREGATION BY WAY OF MOLECULAR NETWORK

(71) Applicants: Charles Jianping Zhou, Mountain View, CA (US); Emily Rong Zhou, Mountain View, CA (US)

(72) Inventors: Charles Jianping Zhou, Mountain View, CA (US); Emily Rong Zhou, Mountain View, CA (US)

( * ) Notice: Subject to any disclaimer, the term of this patent is extended or adjusted under 35 U.S.C. 154(b) by 351 days.

(21) Appl. No.: 14/856,349

(22) Filed: Sep. 16, 2015

(65) Prior Publication Data

US 2017/0076041 A1    Mar. 16, 2017

(51) Int. Cl.
| G06F 7/00 | (2006.01) |
| G16B 50/00 | (2019.01) |
| G06F 16/951 | (2019.01) |
| G06F 16/901 | (2019.01) |
| G16B 5/00 | (2019.01) |
| G06F 16/33 | (2019.01) |

(52) U.S. Cl.
CPC ......... *G16B 50/00* (2019.02); *G06F 16/9024* (2019.01); *G06F 16/951* (2019.01); *G16B 5/00* (2019.02); *G06F 16/3344* (2019.01)

(58) Field of Classification Search
CPC .................................................. G06F 16/3344
USPC ....................................................... 707/692
See application file for complete search history.

(56) References Cited

U.S. PATENT DOCUMENTS

| 6,493,637 | B1* | 12/2002 | Steeg | G06F 17/2715 |
| | | | | 702/19 |
| 6,597,996 | B1* | 7/2003 | Venkataraman | C07K 1/00 |
| | | | | 702/27 |
| 7,358,502 | B1* | 4/2008 | Appleby | G03B 42/04 |
| | | | | 250/370.14 |
| 7,472,121 | B2* | 12/2008 | Kothari | G06F 17/2211 |
| 7,724,257 | B2 | 5/2010 | Smith et al. | |
| 8,015,162 | B2* | 9/2011 | Henzinger | G06F 16/958 |
| | | | | 707/692 |
| 8,818,732 | B2 | 8/2014 | Kinoshita et al. | |
| 8,930,178 | B2* | 1/2015 | Pestian | G06F 17/2785 |
| | | | | 704/9 |
| 9,018,506 | B1 | 4/2015 | Zhou et al. | |
| 9,751,294 | B2* | 9/2017 | Smith | G06F 17/50 |

(Continued)

*Primary Examiner* — Eliyah S. Harper
(74) *Attorney, Agent, or Firm* — Plager Schack LLP; Mark H. Plager; Stephen Hallberg (57) ABSTRACT

A molecular network-based web search and information aggregation system and a process for creating a synthetic molecular network are disclosed. The amount of information and data available through the Internet is growing rapidly, yet current search through natural language-based keyword and page rank algorithm or directory search often cannot provide satisfactory relevant results. The process creates the synthetic molecular network according to a set of rules and chemistry knowledge. The synthetic molecular network is structured such that molecular information can be aggregated in ways that conform to contemporary graphing theory and chemistry rules. In this way, the molecular network-based web search and information aggregation system reduces reliance on natural language by leveraging strong relational associations between molecules that do not correlate to a set of natural language keywords.

11 Claims, 5 Drawing Sheets

(56) References Cited

U.S. PATENT DOCUMENTS

| | | | | |
|---|---|---|---|---|
| 10,025,774 | B2* | 7/2018 | Coulet | G16B 50/00 |
| 2008/0152217 | A1* | 6/2008 | Greer | G06N 3/04 |
| | | | | 382/155 |
| 2008/0281864 | A1* | 11/2008 | Itai | G16B 45/00 |
| 2009/0179147 | A1* | 7/2009 | Milgram | G01N 30/8651 |
| | | | | 250/282 |
| 2010/0070448 | A1* | 3/2010 | Omoigui | H01L 27/1463 |
| | | | | 706/47 |
| 2012/0075325 | A1* | 3/2012 | Kurtyka | G16B 45/00 |
| | | | | 345/589 |
| 2012/0330869 | A1* | 12/2012 | Durham | G06N 5/022 |
| | | | | 706/16 |
| 2014/0156679 | A1* | 6/2014 | Tolbert | G06F 21/62 |
| | | | | 707/749 |
| 2015/0066483 | A1* | 3/2015 | Zhang | G06F 17/278 |
| | | | | 704/9 |

\* cited by examiner

WEB SEARCH AND INFORMATION AGGREGATION BY WAY OF MOLECULAR NETWORK

BACKGROUND

Embodiments of the invention described in this specification relate generally to information search and retrieval, and more particularly, to a system and a method for performing web search and information aggregation via molecular network.

An abundance of information exists as digital data that can be searched for or retrieved from many data sources or repositories. For instance, the amount of information and data available through the Internet is growing rapidly and, as a result, any given web search may retrieve a huge set of search results associated with a wide array of different websites and/or web-connected databases. Much or most of this information and data exist in a common language format (e.g., a website with text information in English or Chinese). Existing information searches, such as web searches, are based on common language search terms, phrases, or keywords (hereinafter referred to as "keyword" or "keywords"). A keyword search, in general, identifies information containing the keyword or a related word/phrase that is associated with the keyword. While information in natural language format is typically easy for a human reader to comprehend, such information is not structured for easy understanding by machines or computers.

Keyword-based web searches often fail to identify closely-related information or data which does not include one or more of the keywords used in the search. In some cases, there are few or no natural language keywords that correlate to certain types of information. This is problematic in fields which have defined strong relational associations between different information and which may depend on one or more aspects of the information that do not correlate to a set of natural language keywords.

Therefore, what is needed is a way to perform a common language keyword-based search for information according to a set of well-defined rules and relationships to make web search more intelligent and efficient and to provide more relevant search results.

BRIEF DESCRIPTION

Some embodiments of the invention include a novel molecular network-based web search, data curation and information aggregation system and a method for creating a molecular network that provides efficient web search and relevant information aggregation.

In some embodiments, the molecular network-based web search and information aggregation system comprises server computers and databases of registered chemical molecules. The databases store data and meta-data about the registered chemical molecules, including (i) an index of the registered chemical molecules, (ii) a URL link for each registered chemical molecule, or (iii) individual molecular information relating to one or more of the registered chemical molecules.

Individual molecular information about a registered chemical molecule includes anything related to, but not limited to, an ID of the registered molecule, a molecular formula, a molecular structure, physical, biological and chemical properties of the molecule, synthesis, applications (as starting material or component of a product), relevant publications in any form (text, graphic, sound, or video) and publication source, author, etc.

In some embodiments, the system is a multi-tiered web application system comprising a user interface (UI) layer, a graph data structure layer, and a database layer. In some embodiments, the multi-tiered web application system includes a hash table layer between the UI layer and the graph data structure layer.

In some embodiments, online information categorization, aggregation, and web page ranking are performed according to all contemporary network data analysis theory, methods, and algorithms and in relation to a synthetic molecular network infrastructure that allows for efficient searching and browsing for relevant information.

In some embodiments, the method for creating the molecular network is performed by one or more computing devices of the molecular network-based web search and information aggregation system. In some embodiments, the method for creating the molecular network is implemented as a software application that runs on a processor of a computing device. In some embodiments, the molecular network is equal to molecular reaction paths (not functional paths currently used in many biological DNA, RNA, and protein mappings): synthetic or metabolic. Data curation and/or information aggregation can be based on reactive and functional molecular network, according to well defined rules and relationships. For any search which can be mapped to molecular level, where "synthetic molecular network" or "synthetic molecular map" can be created with chemistry knowledge on molecular reactions. In this way, information aggregation can be more easily done through the created molecular network or molecular map to provide value added services such as education and learning, focused or directed advertising, online purchasing, etc.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following description, numerous details are set forth for the purpose of explanation. However, one of ordinary skill in the art will realize that the invention may be practiced without the use of these specific details. In other instances, well-known structures and devices are shown in block diagram form in order not to obscure the description of the invention with unnecessary detail.

As stated above, a huge amount of digital data information can be searched for (e.g., web searches) and/or retrieved (e.g., from web sites, database sources, databases, data repositories, etc.) via natural language formatted searches (e.g., keyword or phrase search). The search results of natural language keyword-based searches typically include natural language content that allows most human readers to comprehend with little effort. In contrast to the relative ease with which a human reader is able to parse a set of natural language-oriented search results, such search results are not easy for machine or computer learning, web search algorithms, or web search ranking.

Embodiments of the invention described in this specification solve such problems by a molecular network-based web search and information aggregation system and a method that builds an information network, via molecular reaction map (or molecular network), that is structured according to a set of molecular mapping rules which make it easier for a machine or a computer to process information aggregated as a result of performing a web search via the molecular network.

The molecular network-based web search and information aggregation described in this specification differs from and improves upon currently existing natural language-based web search and information retrieval options because by being based on key words, the existing search options are good only for information not related to molecules or atoms. In contrast, the molecular network-based web search and information aggregation system and process of the present disclosure is excellent at searching the many varied molecules and atoms in the chemical world.

In addition, embodiments of the molecular network-based web search and information aggregation system and process improve upon existing functional molecular networks, which do not provide good relationship information between molecules of these networks. Specifically, embodiments of the molecular network-based web search and information aggregation system and process create a synthetic molecular network that is built on chemical reaction paths with well-defined rules and relations.

In this specification, there are several descriptions of methods and processes that are performed by software running on a computing device (e.g., server computing device that creates a molecular network that allows for web search and information aggregation via the molecular network). However, it should be noted that for the purposes of the embodiments described in this specification, the word "method" is used interchangeably with the word "process". Methods performed by the software are described, therefore, by reference to example processes that are described in further detail below.

Several more detailed embodiments are described in the sections below. Section I describes an architecture of a molecular network-based web search and information aggregation system. Section II describes processes for creating a molecular network graph. Section III describes examples of user interfaces for performing a molecular network-based web search. Section IV describes an electronic system with which some embodiments of the invention are implemented.

I. Molecular Network-Based Web Search and Information Aggregation System

A molecule, by definition, is the smallest particle of a substance that retains the chemical and physical properties of the substance and is composed of one or more atoms. Molecules are the basic units of both living and nonliving matter. Most molecules within living beings, like DNA and protein, although large (known as macromolecules), do not differ in a fundamental way from the molecules of inert matter.

In some embodiments, the molecular network-based web search and information aggregation system comprises server computers and databases of registered chemical molecules that store molecular data comprising one or more of (i) information about at least one registered chemical molecule, (ii) an index of the registered chemical molecules, and (iii) a URL link for each registered chemical molecule.

The information about a registered chemical molecule includes anything related to, but not limited to, an ID of the registered molecule, a molecular formula, a molecular structure, physical, biological and chemical properties of the molecule, synthesis, applications (as starting material or component of a product), relevant publications in any form (text, graphic, sound, or video) and publication source, author, etc.

In some embodiments, the molecular network-based web search and information aggregation system is implemented as a multi-tiered web application system comprising a user interface (UI) layer, a graph data structure layer, and a database layer. In some embodiments, the multi-tiered web application system includes a hash table layer between the UI layer and the graph data structure layer. By way of example, FIG. 1 conceptually illustrates a block diagram of a molecular network-based web search and information aggregation system 100. As shown in this diagram, the molecular network-based web search and information aggregation system includes a user interface (UI) layer 120, a graph data structure layer 130, and a database layer 135. User interfaces are built for data and information management, search and information representation. The UI layer includes different types of user interfaces which allow for a variety of search and browsing interface options. User interfaces can represent graphs in a variety of manners, including, without limitation, graphic based, web based, and text based. Thus, the user interfaces shown in this example include a graphical user interface (GUI) 105, a web user interface (WUI) 110, and a text user interface (TUI) 115.

Figure 1:
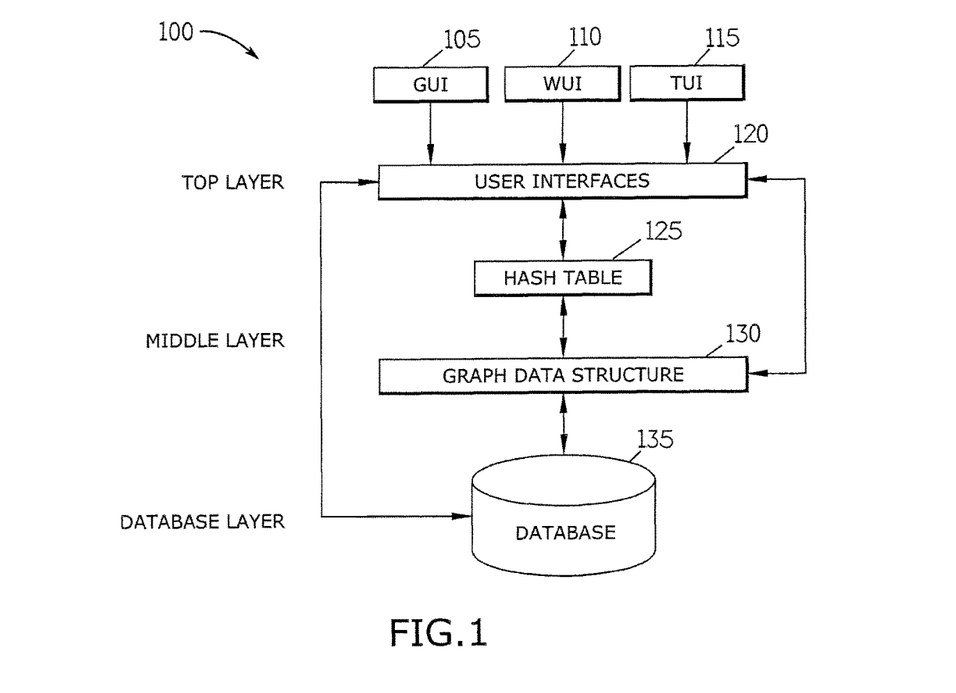
FIG. 1 conceptually illustrates a block diagram of a molecular network-based web search and information aggregation system in some embodiments.

Below the user interfaces of the top layer in FIG. 1 is a hash table 125. The hash table 125 is built based on indexed graph nodes and edges for performance enhancement. For instance, performing several web searches over the molecular network-based web search and information aggregation system 100 would result in several synthetic molecular maps being created in support of those web searches. All such graph nodes and graph edges in the molecular maps would have been previously stored in the molecular chemical database 135 with hash table 125 references to the indexes associated with graph nodes and graph edges.

Unlike a functional molecular network, a synthetic molecular network (SMN) or synthetic molecular map (SMM) is created by following the synthetic chemical scheme of the molecules. Online information categorization, aggregation, and web page ranking are made through utilizing synthetic molecular network infrastructure and all network data analysis theory, methods and algorithms, which enables users to do efficient searching and browsing for relevant information.

While a synthetic molecular network is constructed differently from a functional molecular network, the synthetic molecular network is relevant to the functional molecular network. For example, macromolecules such as DNA and proteins are made from corresponding monomers, monomers are made from smaller and simpler molecules, and final basic molecules such as carbon dioxide, water, etc., are made from atoms such as Carbon, Oxygen, Hydrogen, etc. Functionally, DNA is linked to RNA, and RNA is linked to Protein. Synthetically, proteins are made from amino acids, while DNA and RNA control how and what proteins are made.

Turning now to the graph data structure 130 (or simply "graph") of FIG. 1 (shown in the middle layer below the hash table 125 and directly above the registered chemical molecular database 135), the discussion above about functional and synthetic molecular network construction informs about the manner of creating the graph, namely, based on the synthetic chemistry of the molecules, with each molecule being represented as a graph node, and the chemical relationship or synthetic path between two molecules being represented as a graph edge.

Figure 2:
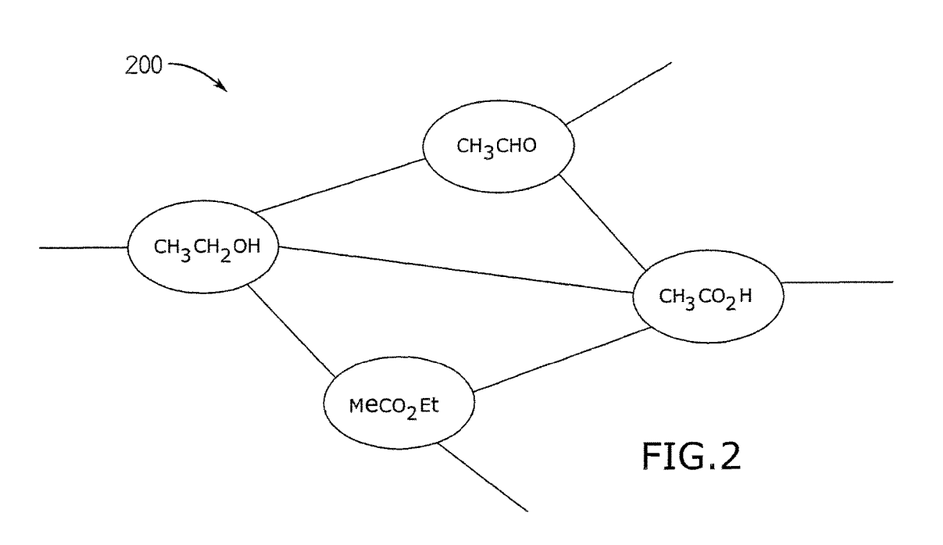
FIG. 2 conceptually illustrates an example of a synthetic molecular network (or synthetic molecular map) in some embodiments.

By way of example, FIG. 2 conceptually illustrates an example of one such molecular network (or molecular map) 200. As shown in this figure, the molecular network/map 200 is represented and managed by utilizing a common graph data structure (as in computer science) for data collection, analysis, and representation. Once it is created, the graph can be represented to the UI layer 120 in at least two ways: (i) map view for easy browsing or (ii) text view for rich information.

Specifically, the graph data structure shown in this figure includes four graph nodes, with each graph node representing a different molecule. Each graph edge between two graph nodes represent the chemical relationship or synthetic path between two molecules that correspond to the graph nodes. Fields may be associated with graph nodes and edges of the graph data structure. Each field (whether associated with a graph node or a graph edge) may include information or links to information elsewhere. However, graph node fields and graph edge fields may not be represented at the UI level 120 or may be hidden from representation until directed to display one or more of the fields. Thus, while no fields are shown in this example, each graph node and each graph edge may include many fields.

II. Processes for Creating a Molecular Network Graph

In some embodiments, one or more processes are performed to utilize the molecular network-based web search and information aggregation system. One such process is for populating molecular chemical databases with relevant information or indexes on known chemical molecules. Populating the molecular chemical databases may be done by search engines via "crawling" and indexing, or manually by user input when needed. In most or even many cases, information in the molecular chemical databases sufficiently relates to all that is known about certain molecules. However, it is possible that a previously "unknown" molecule is identified which does not have any link to any other molecule. In such case, a link or edge can be added when information is available. It is also possible to add a new link or edge to existing links because of updated information. Thus, the next example demonstrates a way to populate the chemical databases.

Figure 3:
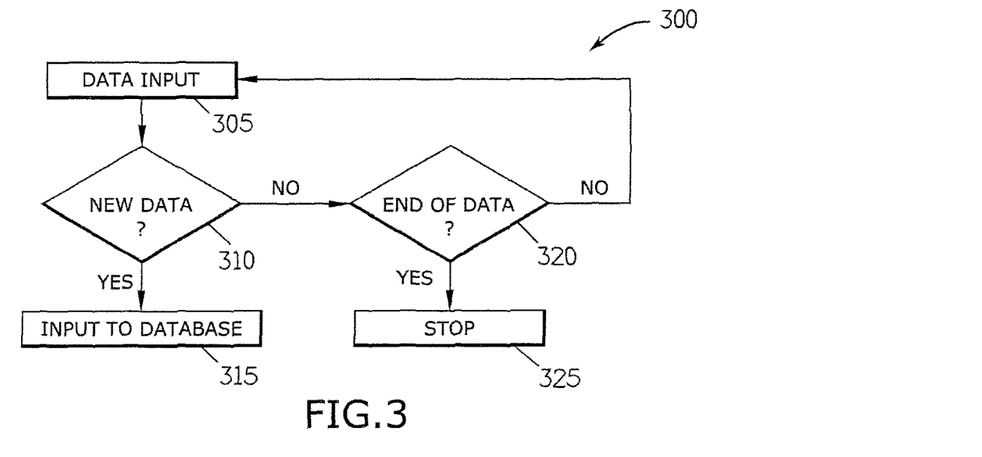
FIG. 3 conceptually illustrates a process for adding data to a database of registered chemical molecules in some embodiments.

FIG. 3 conceptually illustrates a process 300 for adding data to a database of registered chemical molecules. As shown in this figure, the process 300 receives data input (at 305), such as a link between two molecules, a new molecule, or other such information. The process 300 then determines whether the data input is for new data (at 310). When the molecule information is not already in one or more molecular chemical databases, then the process 300 will add the input data to the database (at 315). On the other hand, when the data input is not new, the process determines (at 320) whether to quit (at 325) or whether to accept new data input. When the process accepts new data input, the process 300 repeats (transitioning back to 305). In this way, new molecular information can be supplied to the process 300 to update the chemical databases.

When needed, the information from the database structured as the molecular network or molecular map is retrieved and loaded into the graph data structure. An example of doing this is presented in FIG. 4, which conceptually illustrates a process 400 for creating a molecular network graph data structure. As shown in this figure, the process 400 retrieves data from the database (at 405) and then determines whether the data relates to a graph node (at 410), a graph edge (at 420), or data for links to a node or an edge (at 430). When the process 400 determines that the retrieved data is for a node, an edge, or data for links to a node or an edge, the process 400 then creates the node (at 415), the edge (at 425), or the links (at 435), respectively. The process 400 then determines (at 440) whether more data is to be retrieved. When no more data is to be retrieved, the process 400 ends. On the other hand, when more data exists in the database to be retrieved, the process 400 repeats the process steps described above (transitioning back to 405).

Thus, by mapping possible keyword-based searches or concept searches from natural languages, such as English or Chinese, to concept searches at a molecular level, where a molecular network or map is created according to chemical synthesis rules (e.g., molecular structure, chemical reactions, etc.), the process for creating the molecular network graph data structure is able to provide a graph that is highly structured in ways that allow for manual search and review, as well as automated (e.g., computer-based, machine-based) search and review that is not dependent on the semantic complexity and variation of natural languages.

Once a molecular network graph is created and available, users may interact with the molecular network-based web search and information aggregation system using one or more of the user interfaces (e.g., GUI, WUI, TUI, etc.). Users (human and automated processes and/or electronic devices) may search or browse for information using keywords, ID of molecule, molecular formula, molecular structure in a certain format, etc. Those users with appropriate permissions may input, update, and/or delete certain data, and users with other appropriate permissions may post information, such as papers, advertisements, etc., in a variety of content formats (e.g., audio, video, text, graphics, etc.).

When network infrastructure and all network data analysis theory, methods and representations are applied, online information categorization, aggregation, and resource ranking (e.g., web page, digital content, online papers, etc.) can be efficiently performed by utilizing the created molecular network or map. For example, the link number to one node (molecule) can be used as a ranking criteria for how important the molecule is, as well as how important all of the information related to the molecule is (e.g., synthetic starting material, drug or drug candidate, essential component in living or non-living being, etc.). By way of another example, the shortest path between two nodes (two molecules) in the graph can be used as ranking criteria, such as how important the pathway is in living beings for, e.g., metabolism, or simply to determine the best way to make a molecule. Virtually any node (molecule) or edge (synthetic path or chemical relationship) can be used for information aggregation to provide value added service. For example, if a molecule is commercially available, the vendor's information can be linked as an advertisement, or if the molecule is not commercially available, a custom synthesis service can be linked as an advertisement and provided to the end user. Information on all analytical service and instruments vendors, and others, can also be aggregated via node or edge by links. Also, any section of the graph could be used for information categorization, such as amino acids, alcohols, hydrocarbons, etc.

Figure 4:
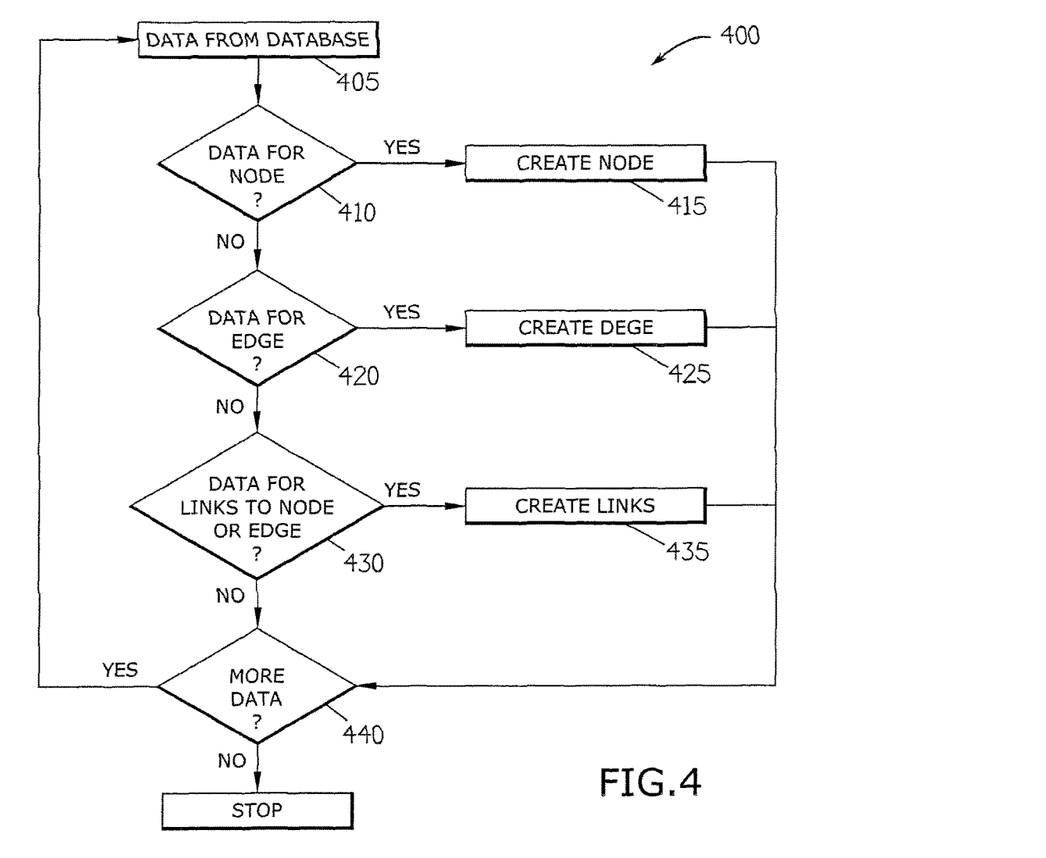
FIG. 4 conceptually illustrates a process for creating a molecular network graph data structure in some embodiments.
Figure 5:
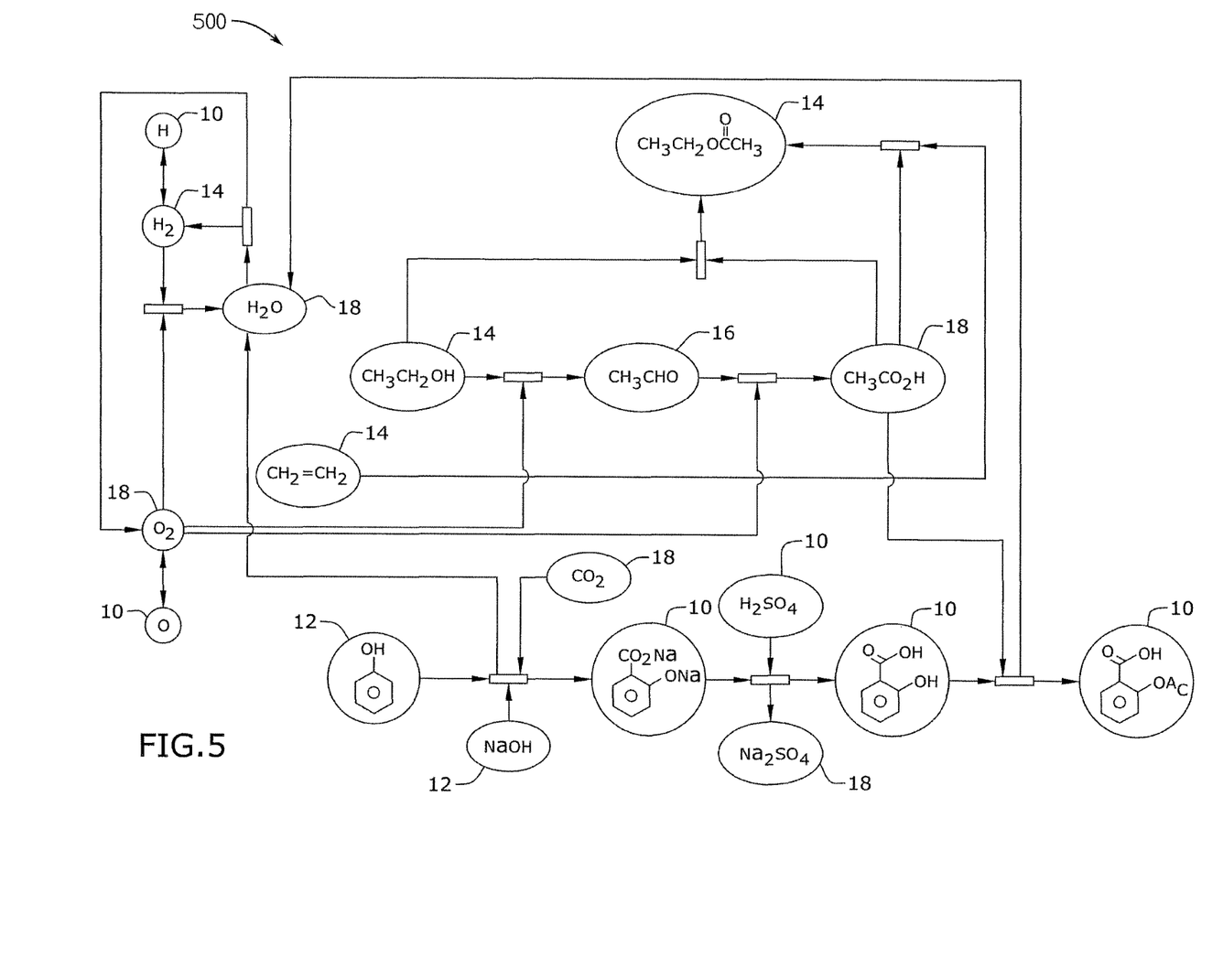
FIG. 5 conceptually illustrates a detailed example of a molecular network graph data structure in some embodiments.

By way of example, FIG. 5 conceptually illustrates a detailed example of a molecular network graph data structure 500 that gets created, for example, by performing the steps of the process 400 described by reference to FIG. 4. In this example, the molecular network graph data structure 500 includes nodes with OSHA safety properties (as determined by the Occupational Safety and Health Administration (OSHA) of the United States. As can be seen, some of the nodes have "unknown" OSHA safety 10 determinations, some other nodes have "health hazard" OSHA safety 12 determinations, other nodes have "storage hazard (flammable)" OSHA safety 14 determinations, yet other nodes have "toxic" OSHA safety 16 determinations, and the remainder of nodes shown in this graph have "environmentally sustainable" OSHA safety 18 determinations.

While the molecular network graph 500 shown in this figure does not show coloring or shading of the nodes, the GUI or WUI may represent the nodes of the graph in different colors in relation to their determined OSHA safety. In this way, a user can quickly search for colors of nodes to identify their relative OSHA safety statuses.

III. Molecular Network-Based Web Search User Interfaces

As described above by reference to FIG. 1, the molecular network-based web search and information aggregation system 100 includes a user interface (UI) layer 120 in which user interfaces allow a user to interact with the system for their search and review needs. A wide variety of user interaction is supported by the UI layer 120. For instance, in representing the molecular network graph described above by reference to FIG. 5, the user may have configured the UI to use the OSHA color-coding scheme so that individual nodes (molecules) of the graph can be quickly reviewed to identify nodes (molecules) which satisfy a specific OSHA safety standard.

The ability to configure the UI as needed provides the user with great power to distinguish between molecules according to their particular needs. For example, if a state law goes into effect banning cleaning agents that are not environmentally sustainable, the user may try to develop a new cleaning agent that is environmentally sustainable and which replaces a particularly effective, but banned, non-abrasive cleaning agent. As such, the user may perform a search with keywords/concept specified as "seeking to make a new non-abrasive cleaning solvent". Without having the benefits of the molecular network-based web search and information aggregation system, the user would need great chemical/molecular knowledge to sift through the search results.

However, by utilizing the molecular network-based web search and information aggregation system, the user could specify the same keywords/concept and the system would transform the search to molecular search according to known rules and structures. Given that the molecular network graph is optimized according to contemporary graph theory and all mapping algorithms, methods, and techniques, the user may quickly hone in on molecules that satisfy or relate to the search criteria (e.g., "seeking to make a new non-abrasive cleaning solvent"). The user would then have the ability to further distinguish the nodes (molecules) of the graph according to the OSHA color-coding safety scheme (e.g., configuring the UI to display the graph according to the OSHA scheme by, for example, selecting the OSHA scheme from a list or a menu). In this way, any user (with or without in-depth knowledge of molecular chemistry) can quickly rule out certain molecules which would not be used and focus only on those which satisfy the current needs of the user.

The UI layer is built to support a wide range of graph representation configurations. Examples of configurations that may be possible in representing the molecular network graph include, without limitation, a map-zooming configuration, an audio search and playback configuration, a video search and playback configuration, etc.

Figure 6:
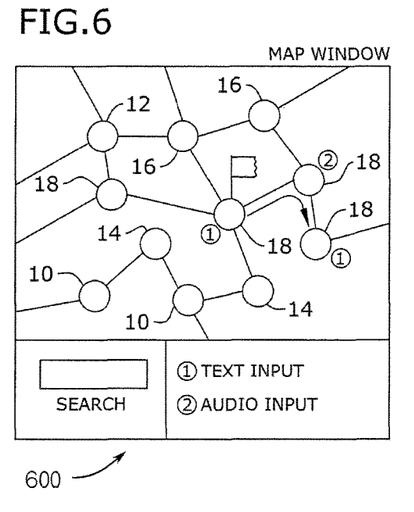
FIG. 6 conceptually illustrates a user interface (UI) with a high level map view of a molecular network graph data structure associated with a search in some embodiments.

By way of example, FIG. 6 conceptually illustrates a user interface (UI) 600 with a map window displaying a high-level view of a molecular network graph data structure associated with a search. As shown in this figure, the map window includes a search tool (displayed with a text input field) and two configurations for specifying enhanced or specific representations of the graph: (1) "TEXT INPUT" and (2) "AUDIO INPUT". A molecular network graph is displayed in the map window above the search tool. The graph includes several nodes (molecules) and several edges (chemical relationships between molecules) between various nodes (molecules).

In this example, the graph representation includes several configurations that allow the display of the graph to distinguish certain desired molecular or chemical criteria. One noteworthy configuration is that the map window shown in FIG. 6 displays the nodes according to a certain weighting that allows the representation to use relative distance as a visual cue. In this way, the graph can be represented to show the importance of one node to another node. That may be important in certain circumstances, such as when it is important to know which molecules are essential for a particular substance, and which molecules are not essential, etc.

Another configuration setting allows for a flag icon to be displayed at a particular node (molecule) which has been identified as most relevant to the search. In some embodiments, a flag icon (or other symbol) can be set to always be displayed in relation to any search, or may be turned off entirely.

Yet another configuration in this example is that the graph is represented according to the OSHA safety color-coding scheme of the graph described above by reference to FIG. 5. (i.e., "unknown" 10, "health hazard" 12, "storage hazard (flammable)" 14, "toxic" 16, "environmentally sustainable" 18).

Additionally, two of the nodes (molecules), including the particular node with the flag and another node to which an arrow is pointing, are associated with a circled reference character "1" and a third node (molecule) in the graph is associated with a circled reference character "2". In this example, the two nodes (molecules) associated with the circled reference character "1" have been selected for representation in text format, and the third node (molecule) associated with the circled reference character "2" has been selected for representation in audio format.

While not shown in the example map window of FIG. 6, some embodiments may also include perspective changing tools, allowing the user to change the map perspective from a top-down view to a "ground level" view, for example. Additionally, some embodiments may include zooming tools, allowing the user to zoom in and out of the graph. For example, the user may wish to zoom in on a particular node (molecule), which causes the map window to enlarge the display of the node (molecule) while changing or removing the display of other features (nodes and/or edges). In some cases, zooming in also causes particular molecule information to be displayed on the node shape (when sufficiently zoomed in). Similarly, if the user zooms out of the map representation, the map window begins to show more and more of the molecular network map, and less of the individual details of the nodes/edges. This may be useful to the user if searching for another section in the graph to focus a search, etc.

Still other molecular network graph representations are possible via the UI layer of the system. Another such representation is provided in FIG. 7, which conceptually illustrates a user interface (UI) 700 for audio search and playback of audible representations of elements in a molecular network graph data structure. This allows for audio search of a synthetic molecular map. For instance, a set of music notes which represent a particular molecule can be input as search criteria, resulting in a display of the molecular network graph data structure centered a node associated with the particular molecule. Additionally, the audio notation (e.g., music notes) can be shown for each node (molecule) during graph traversal. In some embodiments, when a user has selected audio configuration of the UI, an audio window presents an audio tool to play an audio file associated with one or more nodes (molecules) of the molecular network graph data structure. For example, while traversing the visually displayed graph of the molecular network graph data structure, an audio file to play the sound or music representing the molecule at the present node is provided with the audio playback tool. The audio format is useful for some users who need adaptive ways to conceptualize aspects of a molecular network graph. For example, a blind user or a user who has difficulty seeing would be able to comprehend (by, for example, listening to an audio clip with a particular note or sound pattern specific to the structure of a given molecule) the relevant portions of the molecular network graph as represented according to the search.

Figure 7:
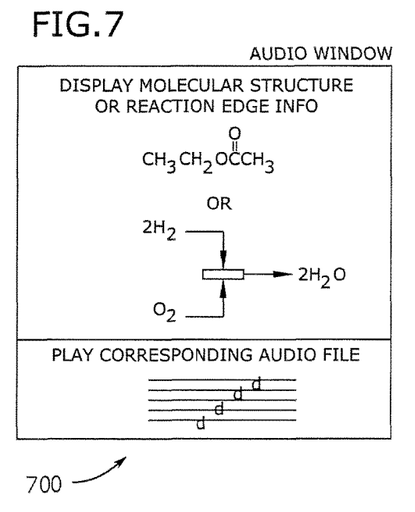
FIG. 7 conceptually illustrates a user interface (UI) with an audio window displaying an audio tool to play an audio file associated with one or more nodes (molecules) of a molecular network graph data structure in some embodiments.

Thus, as shown in FIG. 7, the text representation is displayed above the audio tool, which is associated with a corresponding audio file and includes audible music notes that describe (audibly represent) the structure of the nodes (molecules). Details of audible sound representations of atoms and molecules are described in related U.S. Pat. No. 9,018,506, titled "SYSTEM AND METHOD FOR CREATING AUDIBLE SOUND REPRESENTATIONS OF ATOMS AND MOLECULES" and issued on Apr. 28, 2015. The U.S. Pat. No. 9,018,506 is included herein by reference.

Figure 8:
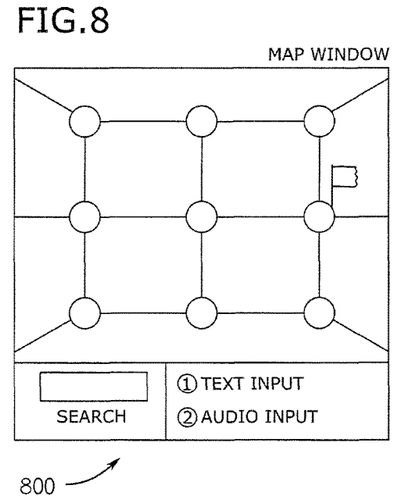
FIG. 8 conceptually illustrates a UI with a grid-style map view of a molecular network graph data structure associated with a search in some embodiments.

Turning to FIG. 8, an organized graph representation is shown in the map window of the user interface (UI) 800. The organized graph representation includes several nodes (molecules) and edges (synthetic relationship between nodes) displayed in a geometric "grid-style" organization. This type of representation is handy to a user in that the node disbursement in the graph is organized according to geometric rules (e.g., right angles, parallel lines for edges, etc.) instead of using a relative distance weighting style, such as the representation of the graph displayed in the map window described above by reference to FIG. 6.

In this case, the organized, geometric "grid-style" display of the graph allows the user to know about the synthetic path or chemical relationship between a particular node and a connected node, but not worry about details such as the relative importance of the particular node in relation to the connected node.

Figure 9:
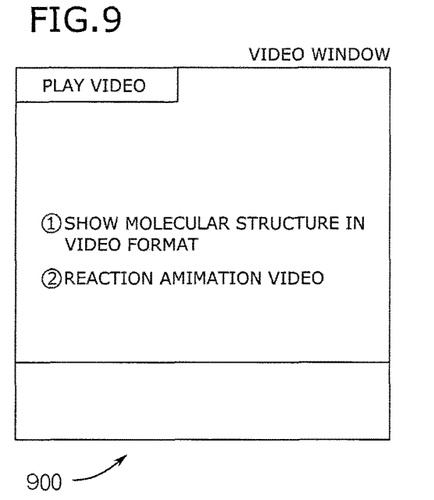
FIG. 9 conceptually illustrates a UI with a video tool to show video of the molecular structure or reaction animation associated with a search in some embodiments.

In FIG. 9, a user interface (UI) 900 with a video tool to show video of the molecular structure or reaction animation associated with a search is shown. The set of visual tools may include corresponding ability to play audio files of molecular structures, while contemporaneously playing the molecular structure video or animation. The playback operations include any of the several well-known playback operations associated with video playback (e.g., play, stop, pause, fast forward, rewind, etc.). Additionally, other such A/V tools are supported in other interfaces.

As these examples demonstrate, the ability to represent the molecular network graph in any of several different configuration styles and manners (according to need), allows a user to tame the data search and information retrieval challenge presented by a molecular network.

IV. Electronic System

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 10:
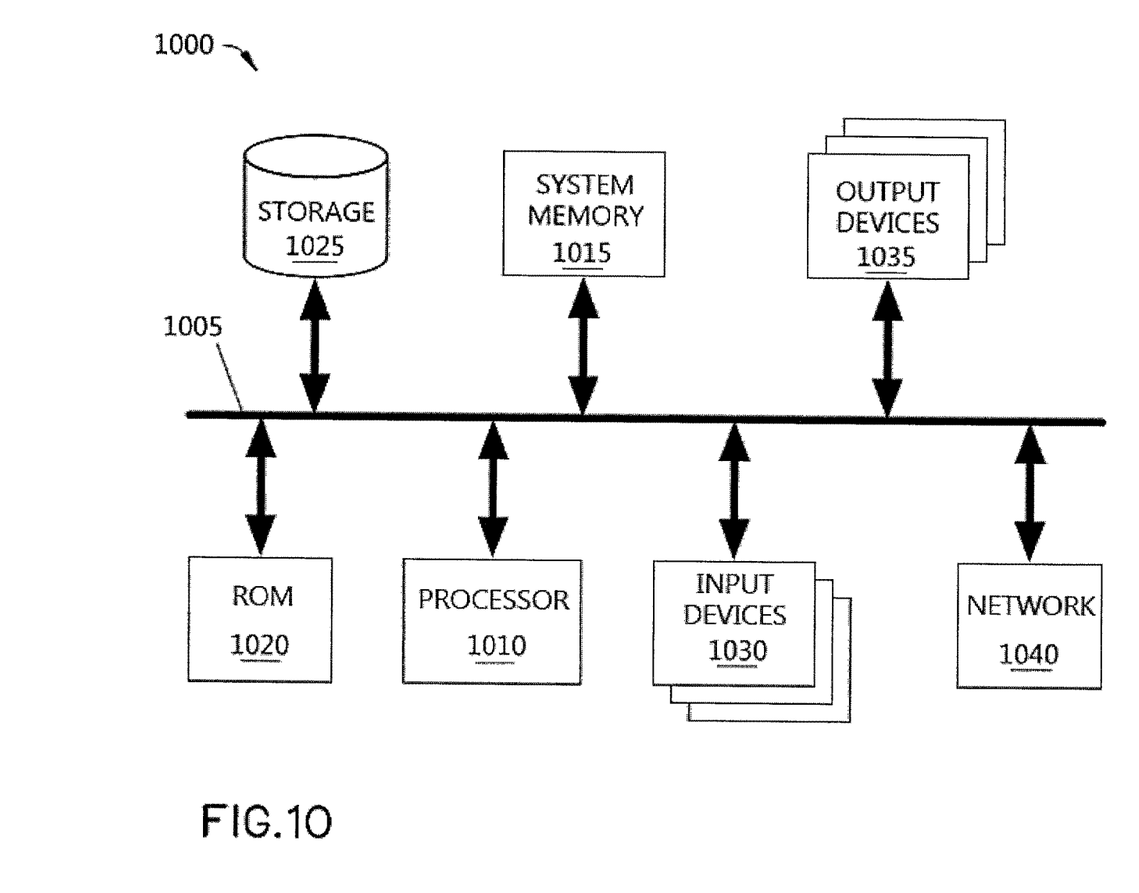
FIG. 10 conceptually illustrates an electronic system with which some embodiments of the invention are implemented.

FIG. 10 conceptually illustrates an electronic system 1000 with which some embodiments of the invention are implemented. The electronic system 1000 may be a computer, phone, PDA, or any other sort of electronic device. Such an electronic system includes various types of computer readable media and interfaces for various other types of computer readable media. Electronic system 1000 includes a bus 1005, processing unit(s) 1010, a system memory 1015, a read-only 1020, a permanent storage device 1025, input devices 1030, output devices 1035, and a network 1040.

The bus 1005 collectively represents all system, peripheral, and chipset buses that communicatively connect the numerous internal devices of the electronic system 1000. For instance, the bus 1005 communicatively connects the processing unit(s) 1010 with the read-only 1020, the system memory 1015, and the permanent storage device 1025.

From these various memory units, the processing unit(s) 1010 retrieves instructions to execute and data to process in order to execute the processes of the invention. The processing unit(s) may be a single processor or a multi-core processor in different embodiments.

The read-only-memory (ROM) 1020 stores static data and instructions that are needed by the processing unit(s) 1010 and other modules of the electronic system. The permanent storage device 1025, on the other hand, is a read-and-write memory device. This device is a non-volatile memory unit that stores instructions and data even when the electronic system 1000 is off. Some embodiments of the invention use a mass-storage device (such as a magnetic or optical disk and its corresponding disk drive) as the permanent storage device 1025.

Other embodiments use a removable storage device (such as a floppy disk or a flash drive) as the permanent storage device 1025. Like the permanent storage device 1025, the system memory 1015 is a read-and-write memory device. However, unlike storage device 1025, the system memory 1015 is a volatile read-and-write memory, such as a random access memory. The system memory 1015 stores some of the instructions and data that the processor needs at runtime. In some embodiments, the invention's processes are stored in the system memory 1015, the permanent storage device 1025, and/or the read-only 1020. For example, the various memory units include instructions for processing appearance alterations of displayable characters in accordance with some embodiments. From these various memory units, the processing unit(s) 1010 retrieves instructions to execute and data to process in order to execute the processes of some embodiments.

The bus 1005 also connects to the input and output devices 1030 and 1035. The input devices enable the member to communicate information and select commands to the electronic system. The input devices 1030 include alphanumeric keyboards and pointing devices (also called "cursor control devices"). The output devices 1035 display images generated by the electronic system 1000. The output devices 1035 include printers and display devices, such as cathode ray tubes (CRT) or liquid crystal displays (LCD). Some embodiments include devices such as a touchscreen that functions as both input and output devices.

Finally, as shown in FIG. 10, bus 1005 also couples electronic system 1000 to a network 1040 through a network adapter (not shown). In this manner, the computer can be a part of a network of computers (such as a local area network ("LAN"), a wide area network ("WAN"), or an intranet), or a network of networks (such as the Internet). Any or all components of electronic system 1000 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIGS. 3-4 conceptually illustrate processes in which the specific operations of each process may not be performed in the exact order shown and described. Specific operations may not be performed in one continuous series of operations, and different specific operations may be performed in different embodiments. Furthermore, each process could be implemented using several sub-processes, or as part of a larger macro process. Thus, one of ordinary skill in the art would understand that the invention is not to be limited by the foregoing illustrative details, but rather is to be defined by the appended claims.

We claim:

1. A non-transitory computer readable medium storing a program which, when executed by at least one processing unit of a computing device, builds a molecular network that is structured according to a set of molecular mapping rules which make it easier for a machine or a computer to process information aggregated as a result of performing a web search via the molecular network, said program comprising sets of instructions for:

receiving a natural language text search from a user computing device operated by a user interested in learning molecular information for a particular chemical-molecular context;

retrieving a set of data from a registered molecule database based on the natural language text search, wherein the set of data comprises information identifying one or more molecules, one or more synthetic chemical relationships between molecules, and data for links of a molecular network graph comprising nodes that represent molecules and edges that represent synthetic chemical relationships between molecules;

creating a node for each identified molecule in the set of data, wherein the node visually represents the identified molecule in the molecular network graph;

for each identified molecule in the set of data, retrieving a corresponding audio clip comprising a sound pattern that aurally represents the identified molecule;

visually marking each node in the molecular network graph to indicate that the audio clip of the corresponding molecule is available for playback with an audio tool that audibly outputs the sound pattern aurally representing the corresponding molecule;

creating an edge for each identified synthetic chemical relationship in the set of data, wherein the edge visually represents the synthetic chemical relationship between two molecules in the molecular network graph;

creating one or more links that visually connect specific nodes in the molecular network graph to specific edges of the molecular network graph;

building a data structure representing the molecular network graph by (i) connecting the created edges to the created nodes according to the links that connect the edges and nodes to represent the molecular network graph, (ii) associating visual marking and visual representations to the corresponding nodes and edges, and (iii) ordering audio clips for audible playback according to one or more node traversal sequences corresponding to the molecular network graph structure;

transmitting the data structure representing the molecular network graph to the user computing device to visually output on a screen of the user computing device in response to the natural language text search to allow the user interested in learning molecular information to view the molecular information of the nodes and edges of the molecular network graph according to the particular chemical-molecular context associated with the natural language text search; and transmitting the ordered audio clips the node traversal sequences of the molecular network graph when audio playback is triggered by selection of the audio tool, wherein the transmitted audio clips are played according to one or more of (i) individual node selection to play the corresponding audio clip and (ii) molecular network graph traversal to play the ordered audio clips according to the node traversal sequence.

2. The non-transitory computer readable medium of claim 1, wherein the molecule is a registered chemical molecule, wherein the node representing the molecule is associated with a set of information about the registered chemical molecule, the set of information comprising an index ID of the registered chemical molecule and at least one of a URL link for the registered chemical molecule and a set of detailed molecular information relating to the registered chemical molecule.

3. The non-transitory computer readable medium of claim 2, wherein the particular chemical-molecular context comprises environmental sustainability, wherein the set of detailed molecular information relating to the registered chemical molecule comprises one or more of a molecular formula, a molecular structure, a set of properties of the molecule including an environmental sustainability property that is set to a particular safety level in a plurality of molecule safety levels, a manner of synthesis, applications, and a relevant publication.

4. The non-transitory computer readable medium of claim 1, wherein the molecule is not a registered chemical molecule, wherein the program further comprises a set of instructions for registering the molecule as a registered chemical molecule.

5. A multi-tiered molecular network-based web search and information aggregation system that provides efficient searching and browsing of relevant chemical and molecular information, said multi-tiered molecular network-based web search and information aggregation system comprising:

a registered chemical molecule database that stores a synthetic molecular network and a plurality of molecular data sets, wherein each molecular data set corresponds to one of a molecule node and a chemical reaction edge of the synthetic molecular network, wherein each molecular data set that corresponds to a molecular node of the synthetic molecular network is associated with a registered chemical molecule in a plurality of registered chemical molecules;

a web application server computer comprising a server processor, a server memory, a server storage, and a software application which when running on the server processor (i) receives natural language search criteria, (ii) transforms the natural language search criteria into a chemical molecule query by a set of chemistry rules, (iii) retrieves a second plurality of molecular data sets from the registered chemical molecule database based on the chemical molecule query, and (iv) generates a molecular network graph comprising a plurality of molecule nodes that correspond to the two or more molecular data sets and a set of chemical reaction edges that each connect two molecule nodes, wherein the molecular network graph is generated by molecule nodes present in the synthetic molecular network and represents a part of the synthetic molecular network; and a client computing device comprising a client processor, a client memory, a client storage, and a software application which when running on the client processor (i) provides a user interface (UI) with a web search input field that allows a user of the client computing device to input natural language search criteria, (ii) transmits the natural language search criteria to the web application server computer to be transformed into the chemical molecule query, and (iii) visually outputs the molecular network graph that represents a part of the synthetic molecular network based on a transformation of the natural language search criteria to the chemical molecule query, wherein the UI further comprises an audio configuration for audio interaction with the web application server computer and the web search input field comprises a set of selectable audio note images, wherein audio note search criteria is transmitted to the web application server computer when the user selects one or more audio note images as input for the web search input field.

6. The multi-tiered molecular network-based web search and information aggregation system of claim 5, wherein the chemical molecule query identifies a particular registered chemical molecule in the synthetic molecular network as a suggested match to the natural language search criteria.

7. The multi-tiered molecular network-based web search and information aggregation system of claim 6, wherein the particular registered chemical molecule corresponds to a particular molecule node in the plurality of molecule nodes of the molecular network graph, wherein at least one other molecule node in the plurality of molecule nodes is directly connected to the particular molecule node by a chemical reaction edge, wherein at least two molecule nodes in the plurality of molecule nodes of the molecular network graph are associated with at least two disjoint molecule nodes in the synthetic molecular network.

8. The multi-tiered molecular network-based web search and information aggregation system of claim 7, wherein the UI comprises a zoom configuration for adjusting a viewable portion of the molecular network graph, said zoom configuration comprising (i) a zoom-in tool which when selected reduces the viewable portion of the molecular network graph and increases a level of detail that is visually output for the viewable molecule nodes and chemical reaction edges and (ii) a zoom-out tool which when selected increases the viewable portion of the synthetic molecular map and decreases the level of detail that is visually output for the viewable molecule nodes and chemical reaction edges.

9. The multi-tiered molecular network-based web search and information aggregation system of claim 5, wherein the UI further comprises a video playback configuration for playback of a video associated with a molecule when the web application server computer returns a molecule associated with a video file in response to the web search query.

10. The multi-tiered molecular network-based web search and information aggregation system of claim 5, wherein the software application running on the server processor of the web application server computer receives the transmitted audio note search criteria and transforms the audio note search criteria into a chemical molecule query by a set of chemistry rules cross referenced with audio note mappings.

11. The multi-tiered molecular network-based web search and information aggregation system of claim 5, wherein each molecular data set comprises one or more of an ID of a registered molecule, a molecular formula of the registered molecule, a molecular structure of the registered molecule, physical properties of the registered molecule, biological properties of the registered molecule, chemical properties of the registered molecule, synthesis of the registered molecule, applications of the registered molecule, and relevant publications about the registered molecule.

* * * * *